United States Patent
Kamataki

(12) 
(10) Patent No.: US 6,660,478 B1
(45) Date of Patent: Dec. 9, 2003

(54) CYP2A6 GENE JUDGMENT METHODS

(75) Inventor: Tetsuya Kamataki, Sapporo (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/959,433

(22) PCT Filed: Apr. 28, 2000

(86) PCT No.: PCT/JP00/02807

§ 371 (c)(1),
(2), (4) Date: Oct. 25, 2001

(87) PCT Pub. No.: WO00/66775

PCT Pub. Date: Nov. 9, 2000

(30) Foreign Application Priority Data

Apr. 28, 1999 (JP) ............................................ 11-122725
Feb. 29, 2000 (JP) .......................................... 2000-52623

(51) Int. Cl.[7] ........................ C07H 21/02; C07H 21/04; C12Q 1/68; C12P 19/34
(52) U.S. Cl. ........................ 435/6; 435/91.2; 536/23.5; 536/23.7; 536/24.31; 536/24.33
(58) Field of Search ................... 435/6, 91.2; 536/23.1, 536/23.5, 23.7, 24.31, 24.33

(56) References Cited

FOREIGN PATENT DOCUMENTS

| JP | A9-187300 | 7/1997 |
| WO | A 95/34679 | 12/1995 |

OTHER PUBLICATIONS

Nunoya et al. Pharmacogenetics. Jun. 1998. 8: 239–249.*
Fernandez–Salguero et al., Am, J. Hum. Genet., vol. 57, pp. 651–660 (1995).
Yamano et al., Biochemistry, vol. 29, pp. 1322–1329 (1990).
Yokoi et al., Pharmaceutical Research, vol. 15, No. 4, pp. 517–524 (1998).
Nunoya et al., The Journal of Pharmacology and Experimental Therapeutics. vol. 289, No. 1, pp. 437–442 (Apr. 1999).
Oscarson et al., FEBS Letters, vol. 448, No. 1, pp. 105–110 (1999).
Nunoya et al., J. Biochem. vol. 126, pp. 402–407 (Aug. 1999).
Fernandez–Salguero, Pedro et al.; "The CYP2A gene subfamily: species . . . " Pharmacogenetics (1995) 5, S123–S128.

* cited by examiner

*Primary Examiner*—Carla Myers
(74) *Attorney, Agent, or Firm*—Birch, Stewart, Kolasch & Birch, LLP

(57) ABSTRACT

There are provided a method of determining a genotype of CYP2A6 gene on the basis of a difference in gene structures of a wild-type gene of CYP2A6 and at least one kind of mutant-type gene associated with mutation of CYP2A6 gene; the method mentioned above, wherein one kind of mutant-type gene associated with mutation of CYP2A6 gene is used, and the mutant-type gene is conversion-type CYP2A6 gene comprising the nucleotide sequence of SEQ ID NO: 4; the method mentioned above, wherein homozygous deletion and heterozygous deletion of CYP2A6 gene are determined by using at least two kinds of mutant-type genes associated with mutation of CYP2A6 gene; a method of determining a genotype of a CYP gene, characterized by carrying out a method comprising the method mentioned above to determine the genotype of the CYP gene; a diagnostic kit for determining a genotype of CYP2A6 gene, comprising 5'-primer capable of hybridizing to both exon 8 of CYP2A6 gene and exon 8 of CYP2A 7 gene, 3'-primer capable of specifically hybridizing to exon 9 of CYP2A6 gene, AccII or an isoschizomer thereof, and Eco81I or an isoschizomer thereof; and the like.

25 Claims, 6 Drawing Sheets

PM ACCATGAGCTTCCTGCCCCGCTGAGCGAGGGCTGTGCCGGTGCAGGTCTGGTGGGCGGGG
   ************************************************************
EM ACCATGAGCTTCCTGCCCCGCTGAGCGAGGGCTGTGCCGGTGCAGGTCTGGTGGGCGGGG

CCAGGGAAAGGCGGGGTCAGGGCGGGGTTCGCGGAAGAGGCGGGTATAAGAATGGGGGGA
   ************************************************************
   CCAGGGAAAGGCGGGGTCAGGGCGGGGTTCGCGGAAGAGGCGGGTATAAGAATGGGGGGA
                                                      Sequence A AGATGCGGGAAAGGAAGGGGCGTGGTGGCTAGAGGGAAGAGAAGAAACAGAAGGGGCTCA
   ************************************************************
   AGATGCGGGAAAGGAAGGGGCGTGGTGGCTAGAGGGAAGAGAAGAAACAGAAGGGGCTCA GTTCACCTTGATAAGGTGCTTCCGAGCTGGGATGAGAGGAAGGAAACCCTTACATTATGC
   ********************* * ************************************
   GTTCACCTTGATAAGGTGCTTCCGTGGTGGGATGAGAGGAAGGAAACCCTTACATTATGC
                        Sequence B TATGAAGAGTAGTAATAATAGCAGCTCTTATTTCCTGAGCACGTACCCCCGTGTCACCTT
   ************************************************************
   TATGAAGAGTAGTAATAATAGCAGCTCTTATTTCCTGAGCACGTACCCCCGTGTCACCTT TGTTCAAAAACCATTGCACGCTCACC      TAATTGCCACAAACCTCTGC      GAA
   ********  **********     ****************      *
   TGTTCAAAAACTATTGCACGCTCACCCACTTAATTGCCACAAACCTCTGCGAAGGGAA GGGCGTTCATGCCCATTTTACACGTGACAAAACTGAGGCTTAGAAAGTTGTCT     TG
   ***************************  *************** *    **
   AAGCGTTCATGCCCATTTTACACGTGACAAAGCTGAGGCTTAGAAAGTTGGCTTATCTG ATGTCTCACAAAACATAAGTGCCCAGAAAATCTTTGAACACAGATC
   **********************************************
   ATGTCTCACAAAACATAAGTGCCCAGAAAATCTTTGAACACAGATC

FIG. 1 a) b)
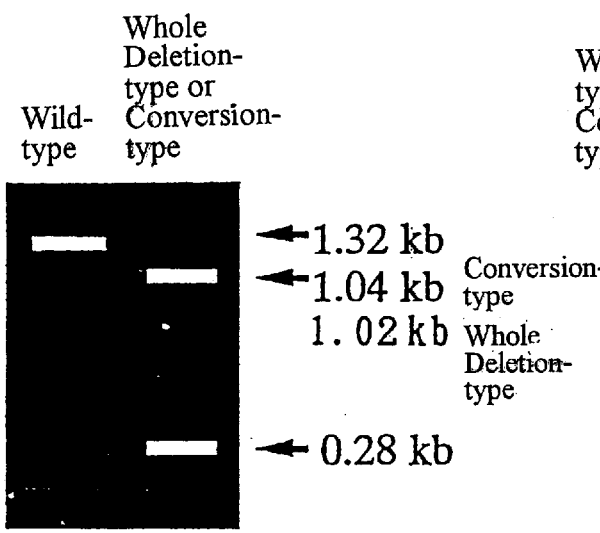 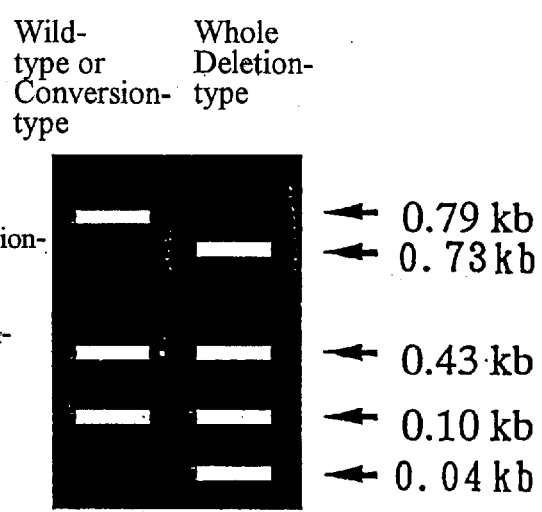
FIG. 5

CYP2A6 GENE JUDGMENT METHODS

This application is the national phase under 35 U.S.C. § 371 of PCT International Application No. PCT/JP00/02807 which has an International filing date of Apr. 28, 2000, which designated the United States of America.

TECHNICAL FIELD

The present invention relates to a method of genotyping CYP2A6 gene, for diagnosing a metabolic ability of a substance which is to be a substrate of human cytochrome P4502A6 (hereinafter abbreviated as CYP2A6) and a diagnostic kit.

BACKGROUND ART

There exists genetic polymorphism in CYP2A6, which has been shown to cause individual differences of the metabolic abilities of the substances which are to be substrates [Japanese Patent Laid-Open No. Hei 9-187300 and *J. Pharmacol. Exp. Trer.* 1999, 289(1): 437–442]. A PAF (platlet-activating factor) receptor antagonist (+)-cis-3,5-dimethyl-2-(3-pyridyl)thiazolidin-4-one (SM-12502) is a representative substrate for CYP2A6, and it has been known that an in vivo metabolic ability of SM-12502 is low in an individual having whole deletion-type mutation of CYP2A6 gene [Japanese Patent Laid-Open No. Hei 9-187300 and *J. Pharmacol. Exp. Trer.* 1999, 289(1): 437–442]. Therefore, it is thought to be very useful that a patient is diagnosed for his/her genotype to previously know the metabolic ability, before administering a drug which is to be a substrate for CYP2A6, such as SM-12502, from the viewpoint of subjecting the patient to an appropriate treatment in accordance with the individual differences of the patient while preventing adverse action.

From the viewpoints described above, the present inventors have so far studied on a method of determining whole deletion-type mutation of CYP2A6 gene. Japanese Patent Laid-Open No. Hei 9-187300 and *J. Pharmacol. Exp. Trer.* 1999, 289(1): 437–442 have suggested deletions of exons 1 to 9 of CYP2A6 gene. Thereafter, by elucidation of the structure of this deletion-type gene, there has been developed a diagnostic method for determining a homozygous deletion individual (the term "homozygous deletion" refers to deletion of both alleles), only summary of the diagnostic method being described in *Pharmaceutical Res.,* 15(4), 517–524, 1998. However, in the diagnosis by this diagnostic method, there arises an unexpected problem that the frequency of a heterozygous deletion individual (the term "heterozygous deletion" refers to deletion of one of alleles) is far higher than a theoretically calculated frequency.

Accordingly, an object of the present invention is to provide a genotyping method of human CYP2A6 gene, for diagnosing a metabolic ability of a substance which is to be a substrate for human CYP2A6 such as SM-12502 in a patient, a diagnostic kit and the like.

DISCLOSURE OF INVENTION

There is a possibility that enzymatic activity is also affected in a case where an individual heterozygously has a whole deletion-type mutation of CYP2A6 gene. Therefore, it is thought that a diagnostic method for accurately determining a heterozygous deletion individual as well as a homozygous deletion individual is necessary, from the viewpoint of giving a patient an appropriate treatment in accordance with individual differences of the patient. Therefore, the present inventors have made various studies on the causation why the frequency of the heterozygous deletion individual is far higher than the theoretically calculated frequency and the like. As a result, there was considered the existence of a new polymorphic gene not reported so far, so that CYP2A6 cDNA was cloned from a human liver sample determined as heterozygote by the above-mentioned old diagnostic method [*Pharmaceutical Res.,* 15(4), 517–524, 1998], and its nucleotide sequence was analyzed. As a result, there was found a new polymorphic gene (hereinafter referred to as "conversion-type") in which there are no mutations in the 5'-untranslational region and the coding region, and a region having a size of about 60 bp in the 3'-untranslational region is converted to a corresponding region of CYP2A7 gene. Here, the term "CYP2A7 gene" refers to another gene of a CYP2A subfamily, which locates on the chromosome 19, the same position as that in CYP2A6 gene, and has high homology to CYP2A6 gene (*Am. J. Hum. Genet.* 57: 651–660, 1995).

There is a possibility that enzymatic activity is also affected in a case where an individual homozygously or heterozygously has a conversion-type mutation of CYP2A6 gene, which is newly found by the present inventors. Therefore, as a result of intensive studies, the present inventors have succeeded in establishing a new diagnostic method capable of genotyping CYP2A6 gene on the bases of the difference in the three kinds of the gene structures, wild-type, whole deletion-type and conversion-type, and the present invention has been perfected thereby.

Specifically, the present invention relates to:

(1) a method of determining a genotype of CYP2A6 gene on the basis of a difference in gene structures of a wild-type gene of human cytochrome P4502A6 (CYP2A6) and at least one kind of mutant-type gene associated with mutation of CYP2A6 gene;

(2) the method according to item (1) above, wherein at least one kind of mutation occurred in the mutant-type gene exists in exon 9 of human cytochrome P4502A7 (CYP2A7) gene, or exon 9 of CYP2A6 gene;

(3) the method according to item (1) above, wherein one kind of mutant-type gene associated with mutation of CYP2A6 gene is used, and the mutant-type gene is conversion-type CYP2A6 gene comprising the nucleotide sequence of SEQ ID NO: 4;

(4) the method according to item (1) above, wherein homozygous deletion and heterozygous deletion of CYP2A6 gene are determined by using at least two kinds of mutant-type genes associated with mutation of CYP2A6 gene;

(5) the method according to item (4) above, wherein the above-mentioned at least two kinds of mutant-type genes associated with mutation of CYP2A6 gene are whole deletion-type CYP2A6 gene comprising the nucleotide sequence of SEQ ID NO: 1 and conversion-type CYP2A6 gene comprising the nucleotide sequence of SEQ ID NO: 4;

(6) the method according to any one of items (1) to (5) above, characterized by analyzing the difference in gene structures by a method comprising PCR method and/or hybridization method;

(7) the method according to any one of items (1) to (6) above, wherein the method comprises the following steps:
   (a) preparing a genomic DNA from a human tissue;
   (b) preparing 5'-primer capable of hybridizing to both exon 8 of CYP2A6 gene and exon 8 of CYP2A7 gene, and 3'-primer capable of specifically hybridizing to exon 9 of CYP2A6 gene;
(c) carrying out amplification reaction by PCR using primers prepared in step (b) as a primer pair, with the genomic DNA prepared in step (a) as a template; and
(d) digesting the amplified product obtained in step (c) with a restriction enzyme, thereby detecting a restriction fragment length polymorphism;
(8) the method according to item (7) above, wherein the 5'-primer has the nucleotide sequence of SEQ ID NO: 5, and the 3'-primer has the nucleotide sequence of SEQ ID NO: 6;
(9) the method according to item (7) or (8) above, wherein the restriction enzyme is AccII or an isoschizomer thereof, and Eco81I or an isoschizomer thereof;
(10) the method according to item (6) above, wherein the method comprises analyzing the difference in gene structures of wild-type CYP2A6 gene and conversion-type CYP2A6 gene, with a DNA fragment having a length of at least 5 bp, the DNA fragment comprising at least one boundary region between CYP2A6 gene and CYP2A7 gene in the nucleotide sequence of SEQ ID NO: 4;
(11) the method according to item (10) above, wherein the method comprises the following steps:
(a) preparing a genomic DNA from a human tissue; and
(b) subjecting the genomic DNA prepared in step (a) or a fragment thereof to hybridization reaction with the DNA fragment having a length of at least 5 bp, the DNA fragment comprising at least one boundary region between CYP2A6 gene and CYP2A7 gene in the nucleotide sequence of SEQ ID NO: 4;
(12) the method according to item (10) or (11) above, characterized in that the DNA fragment is in the form bound to a solid support;
(13) a method of determining a genotype of a CYP gene, characterized by carrying out a method comprising the method of any one of items (1) to (12) above to determine the genotype of the CYP gene;
(14) a conversion-type CYP2A6 gene comprising the nucleotide sequence of SEQ ID NO: 4;
(15) a DNA fragment having a length of at least 5 bp, comprising at least one boundary region between CYP2A6 gene and CYP2A7 gene in the nucleotide sequence of SEQ ID NO: 4;
(16) a DNA fragment having a length of at least 60 bp, comprising two boundary regions between CYP2A6 gene and CYP2A7 gene in the nucleotide sequence of SEQ ID NO: 4;
(17) a solid support with which the DNA fragment of item (15) or (16) above is bound;
(18) a diagnostic kit for determining a genotype of a CYP gene, comprising the DNA fragment of item (15) or (16) above, or the solid support of item (17) above;
(19) a DNA fragment having the nucleotide sequence of SEQ ID NO: 5 or 6;
(20) a diagnostic kit for determining a genotype of CYP2A6 gene, comprising 5'-primer capable of hybridizing to both exon 8 of CYP2A6 gene and exon 8 of CYP2A7 gene; 3'-primer capable of specifically hybridizing to exon 9 of CYP2A6 gene; AccII or an isoschizomer thereof; and Eco81I or an isoschizomer thereof; and
(21) the diagnostic kit according to item (20) above, wherein the 5'-primer has the nucleotide sequence of SEQ ID NO: 5, and the 3'-primer has the nucleotide sequence of SEQ ID NO: 6.

BRIEF DESCRIPTION OF THE DRAWINGS

FIG. 1 shows an alignment of nucleotide sequences of exon 9 of CYP2A7 gene of PM and EM cloned in Example 1, wherein bases in boldface indicate the translational region; Sequences A and B show CYP2A7 gene-specific regions; shaded boxes indicate 3'-UTR-specific, 15 bp deletions in 3'-UTR of CYP2A6 gene.

FIG. 5 is schematic views of a) AccII-RFLP and b) Eco81I-RFLP.

BEST MODE FOR CARRYING OUT THE INVENTION

Figure 2:
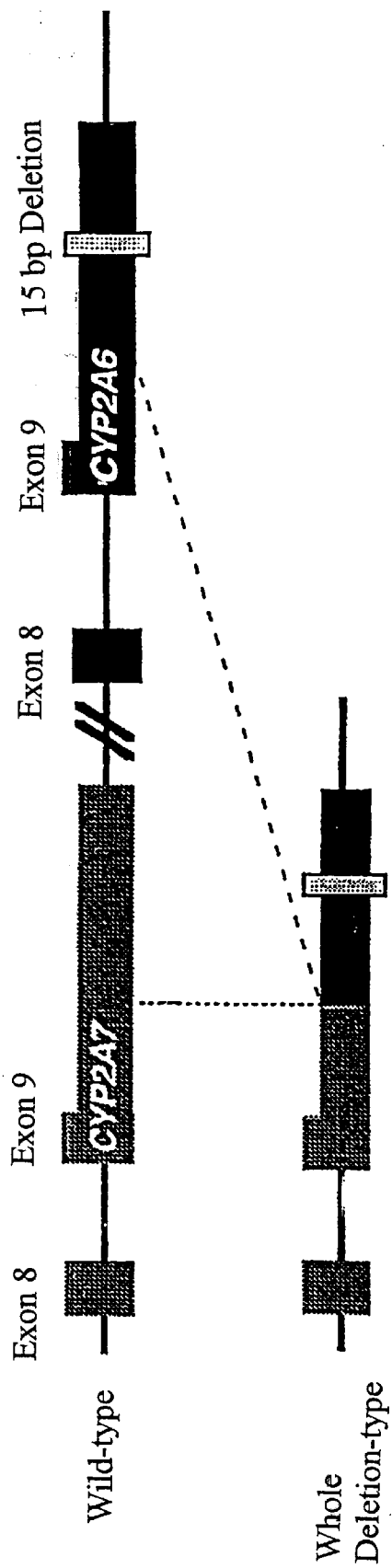
FIG. 2 is a schematic view in which the structures of a wild-type gene and a whole deletion-type gene of CYP2A6 are compared.

The present invention provides a method of determining a genotype of CYP2A6 gene on the basis of the differences in gene structures of a wild-type gene of human cytochrome P4502A6 (CYP2A6), and at least one kind of mutant-type gene, preferably at least two kinds of mutant-type genes, associated with mutation of CYP2A6 gene. In the method of determining a genotype of the present invention, since the structural differences in the three kinds of genes mentioned above can be detected, there is exhibited an excellent effect that, for instance, homozygous deletion and heterozygous deletion can be accurately diagnosed which had been the conventional problem.

CYP2A6 to be genotyped in the genotyping method of the present invention refers to one member of human cytochrome P-450 consisting of superfamily of ubiquitous monooxygenase involved in the metabolism of a wide variety of groups of compounds which are structurally unrelated, including exogenous substrates such as drugs, chemical carcinogens and environmental pollutants, and endogenous substrates such as steroids and fatty acids. A cDNA nucleotide sequence of this gene is described in

*Biochemistry*, 29, 1322–1329, 1990. Coumarin or SM-12502 or the like has been known as the substrate for CYP2A6.

In the present invention, the phrase "wild-type gene of CYP2A6 (wild-type CYP2A6 gene)" refers to a gene having a nucleotide sequence as described in *Biochemistry*, 29, 1322–1329, 1990 mentioned above.

In the present invention, the phrase "at least one kind of mutant-type associated with mutation of CYP2A6 gene" is not particularly limited, as long as the gene comprises at least a partial sequence found in CYP2A6 gene, the gene comprising a nucleotide sequence different from the nucleotide sequence found in a wild-type. Such a gene includes, for instance, a mutant-type CYP2A6 gene comprising a partial sequence of CYP2A7 gene.

Also, in the present invention, the phrase "at least two kinds of mutant-type genes associated with mutation of CYP2A6 gene" is not particularly limited, as long as each gene comprises at least a partial sequence found in CYP2A6 gene, the gene comprising a nucleotide sequence different from the nucleotide sequence found in a wild-type. Such a gene includes, for instance, two or more kinds of mutant-type CYP2A6 genes each comprising a partial sequence of CYP2A7 gene or the like, preferably a whole deletion-type CYP2A6 gene comprising the nucleotide sequence of SEQ ID NO: 1 and a conversion-type CYP2A6 gene comprising the nucleotide sequence of SEQ ID NO: 4. It is preferable to use two kinds of the mutant-type genes for determining homozygous deletion and heterozygous deletion of CYP2A6 genes.

As at least one kind of mutation occurred in the mutant-type gene, one existing in exon 9 of CYP2A7 gene, or exon 9 of CYP2A6 gene is included. Here, the cDNA nucleotide sequence of CYP2A7 gene is described in *Am. J. Hum. Genet.* 57: 651–660, 1995, or GenBank Accession No. U22029.

Concrete examples of the structures of the above-mentioned mutant-type genes include a whole-deletion type gene (whole-deletion type CYP2A6 gene) structure in which CYP2A7 gene is located upstream of CYP2A6 gene, while portions corresponding to 5'-untranslational region and translational region of CYP2A6 gene are deleted, so that the latter half of exon 9 part of CYP2A7 gene (3'-untranslational region, hereinafter abbreviated as "3'-UTR") is directly bonded to 3'-UTR of exon 9 part of CYP2A6 gene; and a conversion-type gene (conversion-type: CYP2A6 gene) structure in which a region having a size of about 60 bp of 3'-UTR of exon 9 of the wild-type CYP2A6 gene is converted to a corresponding region of CYP2A7 gene.

More concretely, as a whole deletion-type CYP2A6 gene, those comprising the nucleotide sequence of SEQ ID NO: 1 are included, and as a conversion-type CYP2A6 gene, those comprising the nucleotide sequence of SEQ ID NO: 4 are included.

Figure 4:
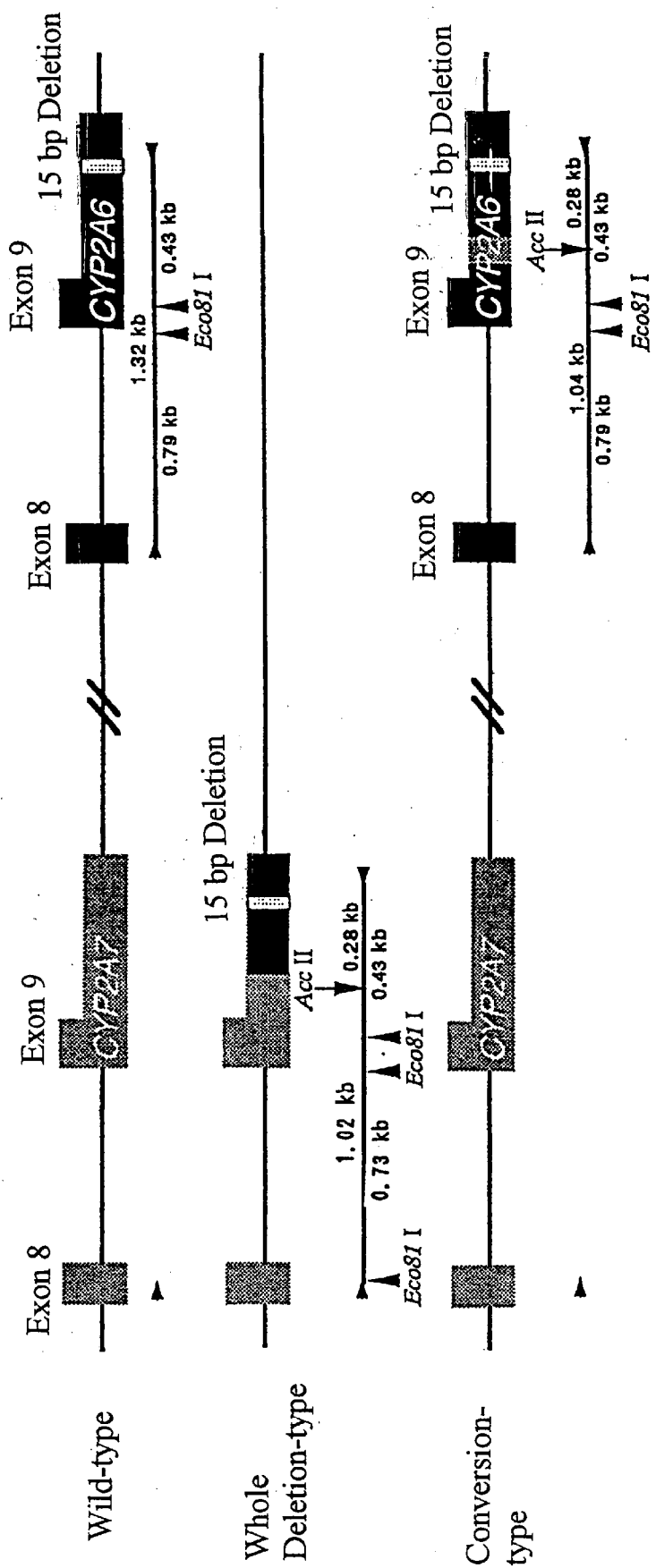
FIG. 4 is a schematic view showing three kinds of CYP2A6 gene structures (wild-type gene structure, whole deletion-type gene structure, and conversion-type gene structure) which can be determined by the genotyping method of the present invention, wherein an arrowhead pointing in the right-hand direction shows the position at which 5'-primer (SEQ ID NO: 5) hybridizes, and an arrowhead pointing in the left-hand direction shows the position at which 3'-primer (SEQ ID NO: 6) hybridizes; a line connecting both arrowheads indicates a region amplified by PCR; an arrowhead in the upward direction indicates a position cleaved by Eco81I; and an arrow indicates a position cleaved by AccII, respectively.

Schematic views of the structures of these whole deletion-type and conversion-type CYP2A6 genes and the wild-type CYP2A6 gene are shown in FIG. 4.

In the present invention, the phrase "the differences in the gene structures" refers to the differences in the nucleotide sequences, such as the differences in exon-intron structures.

The method of determining a genotype of CYP2A6 gene of the present invention has a purpose of, for instance, diagnosing beforehand the function of CYP2A6 (metabolic ability of a substance which is to be a substrate for CYP2A6) in a patient to be subjected to drug administration. In addition, according to one embodiment of the method of determining a genotype of CYP2A6 gene of the present invention, homozygous deletion and heterozygous deletion of CYP2A6 gene can be diagnosed. The determination method is based on the fact that the structures of the mutation sites of the conversion-type CYP2A6 gene and the whole deletion-type CYP2A6 gene have been clarified for the first time in the present invention. According to the determination method of the present invention, a genotype of CYP2A6 gene can be determined by using, for instance, a conversion-type CYP2A6 gene comprising the nucleotide sequence of SEQ ID NO: 4, which is one kind of mutant-type gene associated with mutation of, CYP2A6 gene.

In addition, the determination method of the present invention can be properly constructed by combining techniques usually employed in gene diagnosis [*BIO Clinica* 10(9), 1995, 18–23]. In the determination method, a genotype is determined by analyzing the differences in the gene structures by the method including the techniques.

Concretely, the differences in the gene structures can be analyzed by, for instance, PCR method [*PCR 2: A Practical Approach* (eds. M. J. McPherson, et al.) 1995, IRL Oxford], hybridization method [*Br. J. Haematology* (1990) 75, 73–77], RFLP method [*J. Clinical Investigation* (1985) 76, 1283–1285], SSCP method [*PNAS* (1989) 86, 2766–2770], direct sequencing method [*Science* (1988) 239, 487–491; *Nature* (1987) 330, 384–386], chemical cleavage method of mutant base pairs [PNAS(1988) 85, 4397–4401], DGGE method [*Methods in Enzymology* (1987) 155, 501–527], enzymatic cleavage method of mutant base pairs [*In Genomic Analysis: A Practical Approach* (ed. K. Davies) 95–139, IRL Oxford], mass spectroscopy method [*Nucleic Acids Res.*, 28(5), E13 (2000)], and/or HPLC method [*Genomics*, 56(3), 247–253 (1999); *Hum. Genet.*, 104(1), 89–93, (1999)], and the like. It is preferable to use a method comprising PCR method and hybridization method.

As a representative example of the method of determining a genotype of CYP2A6 gene of the present invention, a determination method utilizing PCR (polymerase chain reaction) will be described hereinbelow.

In the present invention, a determination method comprising amplifying a gene by PCR is employed. PCR includes LA (Long and Accurate)-PCR, and the like.

The method of determining a genotype of CYP2A6 gene after PCR, preferably a method of diagnosing homozygous deletion and heterozygous deletion of CYP2A6 gene includes direct sequencing method, restriction fragment length polymorphism (RFLP) method and the like, and the RFLP method is preferable.

One embodiment of the method of determining a genotype of CYP2A6 gene of the present invention utilizing PCR is a method comprising the following steps:

(a) preparing a genomic DNA from a human tissue;
(b) preparing 5'-primer capable of hybridizing to both exon 8 of CYP2A6 gene and exon 8 of CYP2A7 gene, and 3'-primer capable of specifically hybridizing to exon 9 of CYP2A6 gene;
(c) carrying out amplification reaction by PCR using primers prepared in step (b) as a primer pair, with the genomic DNA prepared in step (a) as a template; and
(d) digesting the amplified product obtained in step (c) with a restriction enzyme, thereby detecting a restriction fragment length polymorphism.

In step (a), a genomic DNA is prepared from a human tissue. The human tissue is not particularly limited, as long as the genomic DNA can be isolated therefrom, and includes blood, thrix, unguis, oral mucosa, liver and the like. The blood is desirable, from the viewpoint of an amount and easiness in preparation.

The method of preparing the genomic DNA can be performed by a conventional method described, for instance, in *Molecular Cloning: A Laboratory Manual*, Cold Spring Harbor Laboratory Press (1989). A commercially available genome extraction kit or the like can be also utilized.

In order to amplify the wild-type gene, the whole deletion-type gene and the conversion-type gene of CYP2A6 mentioned above, in step (b), 5'-primer capable of hybridizing to both exon 8 of CYP2A6 gene and exon 8 of CYP2A7 gene, and 3'-primer capable of specifically hybridizing to exon 9 of CYP2A6 gene are prepared.

With regard to the designing of the primer, it is important to design a primer so that all of the three kinds of genes mentioned above are amplified, while the amplification of genes of other CYP2A subfamilies such as genes of wild-type CYP2A7 and CYP2A13 having high homologies is prevented. One of ordinary skill in the art can appropriately design the primer mentioned above on the basis of the fact that the structures of the mutation sites of the whole deletion-type gene and the conversion-type gene have been clarified for the first time in the present invention.

Here, the term "capable of hybridizing" means that the primer is capable of forming a hybrid with the wild-type gene, the whole deletion-type gene or the conversion-type gene of CYP2A6 mentioned above under the conditions relating to an oligonucleotide for a probe or primer as described, for instance, in *Molecular Cloning: A Laboratory Manual*, 2nd Edition (1989). Since the primer has the characteristics mentioned above, there can be sufficiently exhibited effects so that all of the above-mentioned three kinds of genes are amplified, while preventing the amplification of genes of other CYP2A subfamilies having high homologies, under the PCR amplification conditions as concretely described in Examples described below.

The length of the primer is usually from 10 to 50 bases or so, preferably from 20 to 30 bases or so. Examples of the primer are as follows: 5'-primer includes an oligonucleotide having, or comprising, the nucleotide sequence of SEQ ID NO: 5; and 3'-primer includes an oligonucleotide having, or comprising, the nucleotide sequence of SEQ ID NO: 6. A combination of the oligonucleotide having the nucleotide sequence of SEQ ID NO: 5 with the oligonucleotide having the nucleotide sequence of SEQ ID NO: 6 is preferable.

The primer can be prepared by a conventional method by using a DNA synthesizer.

In step (c), the amplification reaction is carried out by polymerase chain reaction using primers prepared in step (b) as a primer pair, with the genomic DNA prepared in step (a) as a template.

The polymerase chain reaction (PCR) can be performed by a conventional method such as a method described in *Molecular Cloning: A Laboratory Manual* mentioned above. As a DNA polymerase, a commercially available DNA polymerase for PCR can be suitably used, and a polymerase attached to a commercially available PCR kit can be also used. In the present invention, since formation of an amplified product having a size of about 1.3 kb is deduced from the position of the selected primers, it is preferable to use, for instance, LA-PCR kit (manufactured by Takara Shuzo Co., Ltd.) or the like.

The conditions for PCR can be appropriately set depending upon the template, the primers, fragment lengths to be amplified, and the like.

In step (d), the amplified product obtained in step (c) is digested with a restriction enzyme, thereby detecting an RFLP.

Here, it is preferable to select a restriction enzyme so that the digestion by the restriction enzyme produces RFLP with sufficiently taking into consideration of the nucleotide sequence of the amplified product. One of ordinary skill in the art can appropriately select the restriction enzyme on the basis of the fact that the structures of the mutation sites of the whole deletion-type gene and the conversion-type gene have been clarified for the first time in the present invention. As one example, there can be used a restriction enzyme AccII or an isoschizomer thereof, which is capable of cleaving a conversion-type CYP2A6 DNA and a whole deletion-type CYP2A6 DNA each at one site, while not cleaving a wild-type CYP2A6 DNA. Further, there can be used a restriction enzyme Eco81I or an isoschizomer thereof, which is capable of cleaving a whole deletion-type CYP2A6 DNA at three sites, and cleaving a wild-type CYP2A6 DNA and a conversion-type CYP2A6 DNA each at two sites. The cleavage positions of these restriction enzymes are shown by arrows and arrowheads in FIG. 4. Further, other restriction enzymes can be used depending upon the nucleotide sequence of the amplified product.

First, the digestion by the above-mentioned two kinds of restriction enzymes is carried out by placing a part of the amplified product in separate reaction vessels, and digesting the amplified product according to the reaction conditions for the restriction enzymes until the amplified product is completely digested. As the restriction enzyme, a commercially available restriction enzyme can be used, and digestion may be performed in accordance with the attached protocol.

Next, the resulting digested fragment is subjected to electrophoresis to detect RFLPs. The electrophoresis is carried out under usual conditions by using agarose gel or the like used in the separation of DNA. In order to estimate the length of the digested fragment, it is preferable to simultaneously electrophorese commercially available DNA size markers. The electrophoresed DNA fragment is detected, for instance, by visually observing or photographing electrophoretic patterns of DNA in the above-mentioned agarose gel or the like to which ethidium bromide is added, under UV irradiation after electrophoresis, and determining the relative position of a DNA fragment to be detected against the size marker. For instance, as shown in FIG. 5, there are obtained patterns which can distinguish the wild-type CYP2A6 DNA with the conversion-type CYP2A6 DNA or the whole deletion-type CYP2A6 DNA (FIG. 5, *a*, AccII-RFLP); and patterns which can distinguish the wild-type CYP2A6 DNA and the conversion-type CYP2A6 DNA with the whole deletion-type CYP2A6 DNA (FIG. 5, *b*, Eco81I-RFLP).

Finally, the homozygous deletion and heterozygous deletion of CYP2A6 gene are diagnosed on the basis of the above-mentioned two kinds of RFLPs. For instance, as shown in FIG. 6(B), the homozygous deletion (indicated by *4C/*4C in the figure) and the heterozygous deletion (indicated by *1A/*4C and *1B/*4C in the figure) are clearly differentiated with each other. In addition, all genotypes (indicated by *1A/*1A, *1A/*1B, *1B/*1B, *1A/*4C, *1B/*4C and *4C/*4C in the figure) can be clearly differentiated.

Those exemplified above are representative examples of the method of determining a genotype of CYP2A6 gene utilizing PCR.

Figure 3:
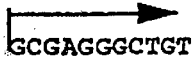
FIG. 3 shows an alignment of nucleotide sequences of a 3'-terminal side of exon 9 of wild-type and conversion-type CYP2A6 genes cloned in Example 2, wherein the underlined part is a characteristic region of CYP2A7 gene.

In the present invention, the "conversion-type CYP2A6 gene" in which a region having a size of about 60 bp of 3'-UTR of the CYP2A6 gene is converted to a corresponding region of CYP2A7 gene has been found for the first time. A partial nucleotide sequence of the conversion-type CYP2A6 gene including the conversion region is shown in SEQ ID NO: 4. Also, the comparison of a partial nucleotide sequence of the conversion-type CYP2A6 gene (SEQ ID NO: 4) with a nucleotide sequence of a region corresponding to the wild-type CYP2A6 gene (SEQ ID NO: 3) is shown in FIG. 3, wherein underlined portion indicates the region converted to CYP2A7 gene. Here, a nucleotide sequence comprising a boundary region between CYP2A6 gene and CYP2A7 gene in the nucleotide sequence of SEQ ID NO: 4 is a sequence which exists in the conversion-type CYP2A6 gene, but not in the wild-type CYP2A6 gene. Therefore, by detecting the presence or absence of the nucleotide sequence comprising at least one boundary region, the differences in the gene structures of the wild-type CYP2A6 gene and the conversion-type CYP2A6 gene can be analyzed. This embodiment is also one embodiment for the determination method of the present invention.

Concretely, there is exemplified a method comprising carrying out PCR, hybridization reaction, mass spectroscopy, HPLC analysis or the like mentioned above by using a DNA fragment comprising at least one boundary region in the nucleotide sequence of SEQ ID NO: 4 as a DNA for diagnosis, thereby analyzing the differences in the gene structures of the wild-type CYP2A6 gene and the conversion-type CYP2A6 gene.

Here, the length of the DNA fragment comprising the boundary region is not particularly limited, as long as the differences of the wild-type CYP2A6 gene and the conversion-type CYP2A6 gene can be detected. The length of the fragment can be properly varied within the range of the common knowledge of the one of ordinary skill in the art, and a DNA fragment has a length of, for instance, at least 5 bp, preferably 25 bp or more to 5 kb or less. In addition, there can be used a DNA fragment having a length of at least 60 bp, comprising two boundary regions between the CYP2A6 gene and the CYP2A7 gene. The DNA fragment may be in the form of a single strand or a double strand depending upon its purposes.

One embodiment of the method of determining a genotype of CYP2A6 gene is a method comprising the following steps:

(a) preparing a genomic DNA from a human tissue; and (b) subjecting the genomic DNA prepared in step (a) to hybridization reaction with the DNA fragment having a length of at least 5 bp, the DNA fragment comprising at least one boundary region between CYP2A6 gene and CYP2A7 gene in the nucleotide sequence of SEQ ID NO: 4.

In step (a), a genomic DNA is prepared from a human tissue. The human tissue is not particularly limited, as long as the genomic DNA can be isolated therefrom, and includes blood, thrix, unguis, oral mucosa, liver and the like. The blood is desirable, from the viewpoint of an amount and easiness in preparation.

The method of preparing the genomic DNA can be performed by a conventional method described, for instance, in *Molecular Cloning: A Laboratory Manual*, Cold Spring Harbor Laboratory Press (1989). Also, a commercially available genome extraction kit or the like can be utilized. The prepared genomic DNA can be optionally labeled with fluorescence or the like by a conventional method. Also, the resulting genomic DNA may be optionally fragmented, or a specified portion thereof may be optionally amplified by PCR or the like, whereby the resulting products can be used in step (b) described below.

In step (b), a DNA fragment having a length of at least 5 bp is used, the DNA fragment comprising at least one boundary region between CYP2A6 gene and CYP2A7 gene in the nucleotide sequence of conversion-type CYP2A6 gene of SEQ ID NO: 4. Here, the length and the form of the DNA fragment are as described above, and one of ordinary skill in the art can appropriately design the fragment on the basis of the fact that the structure of the conversion-type gene has been clarified for the first time in the present invention. Especially, in step (b), a DNA fragment having a size of about 25 bp or more to about 5 kb or less is preferably used. These DNA fragments can be prepared by a conventional method by using a DNA synthesizer. In addition, the DNA fragment can be optionally labeled with fluorescence or the like.

Using the DNA fragment, the hybridization reaction with the genomic DNA prepared in step (a) or a fragment thereof is carried out. Here, the conditions for hybridization include usual conditions described in the above-mentioned *Molecular Cloning* or the like. Besides them, any conditions can be used, as long as a completely complementary sequence and a sequence comprising a partially different nucleotide sequence can be distinguished in the conditions.

The above-mentioned DNA fragment can be also used in the form bound to a solid support. Here, the solid support refers to glass, silicon surface, nitrocellulose filter, nylon membrane, or the like. Recently, there can be carried out diagnosis and determination using a so-called DNA chip in which a DNA fragment is bound to the solid support mentioned above. In this case, it is preferable that a genomic DNA to be tested is fragmented, and labeled with fluorescence or the like. The above-mentioned determination can be carried out by hybridizing the genomic DNA with the DNA fragment on the solid support, and detecting the fluorescence on the solid support. Here, the DNA fragment-bonded DNA chip is available through an order made to Affimetrix, U.S.A., and a concrete means for the above-mentioned determination method can be referred to *Nature Genetics*, 21, 1–60 (1999), and the like.

The method of determining a genotype of CYP2A6 gene described above is utilized in the method of determining a genotype in entire CYP genes. Therefore, the present invention provides a method of determining a genotype of a CYP gene, wherein the determination of a genotype of a CYP gene is carried out by the method comprising any one of the above-mentioned determination methods.

Further, the present invention provides a DNA for diagnosis and a solid support for diagnosis which are used in the method of determining a genotype of CYP2A6 gene mentioned above. In addition, the present invention provides a diagnostic kit comprising the DNA for diagnosis or the solid support for diagnosis mentioned above.

Concrete examples of the diagnostic kit are given below.

1) A diagnostic kit comprising a DNA fragment having a length of at least 5 bp, comprising at least one boundary region between CYP2A6 gene and CYP2A7 gene in the nucleotide sequence of SEQ ID NO: 4; a DNA fragment having a length of at least 60 bp, comprising two boundary regions between CYP2A6 gene and CYP2A7 gene in the nucleotide sequence of SEQ ID NO: 4; or a solid support with which the DNA fragment mentioned above is bound.

2) A diagnostic kit comprising 5'-primer capable of hybridizing to both exon 8 of CYP2A6 gene and exon 8 of CYP2A7 gene; 3'-primer capable of specifically hybridizing to exon 9 of CYP2A6 gene; restriction enzyme AccII or an isoschizomer thereof; and restriction enzyme Eco81I or an isoschizomer thereof.

Here, the preferred example of the diagnostic kit of item 2) above is a diagnostic kit of the following item 3).

3) A diagnostic kit comprising 5'-primer having the nucleotide sequence of SEQ ID NO: 5; 3'-primer having the nucleotide sequence of SEQ ID NO: 6; AccII or an isoschizomer thereof; and Eco81I or an isoschizomer thereof.

5'-primer and 3'-primer, and restriction enzymes AccII, Eco81I and isoschizomers thereof contained in the above-mentioned kit are as defined above. In addition, the above-mentioned kit may further comprise a DNA polymerase for carrying out PCR, buffer for PCR, buffer for restriction enzyme reaction, and the like.

The kit of the present invention is used for conveniently and accurately carrying out the diagnosis method of the present invention.

The present invention will be described by means of Examples hereinbelow, without intending to limit the scope of the present invention thereto.

Example 1

Structural Analysis of Whole Deletion-Type CYP2A6 Gene

Genomic DNA was extracted from peripheral blood of a subject deduced to be EM (extensive metabolizer) and a subject deduced to be PM (poor metabolizer) (Japanese Patent Laid-Open No. Hei 9-187300), on the basis of determination of the concentration of SM-12502 in the blood in accordance with a conventional method (Sambrook et al., *Molecular Cloning: A Laboratory Manual,* 2nd Edition, Cold Spring Harbor Laboratory Press, 1989). Thereafter, the resulting genomic DNA was digested partially with Sau3AI, and fractionated by a sucrose density gradient (10–38%) centrifugation. The fraction containing a fragment having a size of about 15 kb was partially filled-in with dGTP and dATP, and ligated to a lambda FIXII vector (Stratagene), which had been previously digested with XhoI and partially filled-in with dTTP and dCTP. Subsequently, the ligation product was packaged in vitro using Gigapack III Gold Packaging Extracts. CYP2A6 genes of PM and EM and CYP2A7 genes located upstream thereof were cloned from the genomic library prepared as described above with a CYP2A6 cDNA fragment having a size of 1.6 kb as a probe, and their nucleotide sequences were determined by the dideoxy method with Sequenase Ver.2 (manufactured by United States Biochemical Co.) or Applied Biosystems Model 373A DNA Sequencer in accordance with the protocol provided by the manufacturer. A cDNA fragment of human CYP2A6 having a size of 1.6 kb, which was used as a probe, was prepared by the method described in Japanese Patent Laid-Open No. Hei 9-187300.

As a result, it was clarified that in CYP2A7 gene of PM, the latter half of exon 9 portion (3'-UTR) was ligated (directly bonded) to 3'-UTR of CYP2A6 gene. The nucleotide sequence of this ligating region and the region before and behind the ligating region is shown in FIG. 1 and SEQ ID NO: 1 (PM), and the nucleotide sequence of the corresponding region in EM is also shown in FIG. 1 and SEQ ID NO: 2 (EM). Since both of Sequences A and B of FIG. 1 are CYP2A7 gene-specific sequence portions, it was shown that ligation was carried out somewhere between Sequences A and B in PM. Specifically, only 3'-UTR of CYP2A6 gene existed in PM, so that it was clarified that CYP2A6 gene had a structure where 5'-UTR and translational region of the gene were wholly deleted. The comparisons (schematic views) of the gene structure of this whole deletion-type CYP2A6 (CYP2A6*4C) and the gene structure of wild-type CYP2A6 (CYP2A6*1A) (*Biochemistry,* 29, 1322–1329 (1990)) are shown in FIG. 2.

Example 2

Structural Analysis of Conversion-type CYP2A6 Gene

Utilizing the difference in the gene structures of the whole deletion-type gene identified in Example 1 mentioned above and the wild-type gene, a method capable of diagnosing a homozygous individual with whole deletion-type gene (homozygous deletion individual) was developed (only summary of the diagnostic method being described in *Pharmaceutical Res.,* 15(4), 517–524, 1998). However, in this diagnostic method, the heterozygous deletion individual cannot be diagnosed, and as causation thereof, the presence of a new polymorphic gene which had not been reported so far was suggested. Therefore, the following experiment was carried out for the purpose of cloning this new polymorphic gene.

Whole RNA was prepared by guanidinium-thiocyanate method, a conventional method, from the liver of human judged as heterozygous deletion. Six micrograms of the whole RNA was subjected to reverse transcription by using MMLV reverse transcriptase (0.2 units, manufactured by TOYOBO CO., LTD.) with random hexamers (120 ng, manufactured by Pharmacia) as primers in 30 μl of the reaction solution. By using the combination of the designed primers for the sequence reported in *Biochemistry,* 29, 1322–1329, 1990, CYP2A6 cDNA was obtained by RT-PCR. All of the resulting clones were subcloned in pBluescript SK(−) vector (manufactured by Stratagene), and their nucleotide sequences were determined by using Applied Biosystems Model 377A Automatic DNA Sequencer. As a control, CYP2A6 cDNA prepared from whole RNA derived from the liver of human whose genotype was judged as homozygous wild-type was also cloned in the same manner, and the nucleotide sequence was determined.

The above-mentioned heterozygous deletion CYP2A6 cDNA was compared with wild-type CYP2A6 cDNA. As a result, it was clarified that heterozygous deletion CYP2A6 cDNA has a novel sequence in which about 60 bp of 3'-UTR is converted to a corresponding region of CYP2A7, while 5'-UTR and protein coding region have the same sequences as those of the wild-type. The nucleotide sequence of this conversion site and the region before and behind the conversion site is shown in FIG. 3 and SEQ ID NO: 4 (conversion-type), and the nucleotide sequence of the corresponding region in the wild-type is also shown in FIG. 3 and SEQ ID NO: 3 (wild-type).

Example 3

Development of Novel Genotyping Method for CYP2A6 Gene

A novel diagnostic method capable of differentiating individuals homozygously or heterozygously having these three types of genes was developed, based on comparison of the whole deletion-type gene structure and the conversion-type gene structure of CYP2A6 gene identified in Examples 1 and 2 with those of the wild-type gene.

a) Preparation of Genomic DNA

There can be utilized genomic DNA extracted from peripheral blood in an amount of at least 0.1 ml or so by using a commercially available genome extraction kit (one manufactured by Takara Shuzo Co., Ltd. and the like).

b) Primers

The following primers:

CYP2A6-B4 5'-CAC CGA AGT GTT CCC TAT GCT G-3' (SEQ ID NO: 5)

CYP2A6-UTRAS1 5'-TGT AAA ATG GGC ATG AAC GCC C-3' (SEQ ID NO: 6)

are synthesized by using a DNA synthesizer, and the primers are dissolved in Tris-EDTA buffer (pH 7.4), and thereafter the solution is diluted with sterilized water to a concentration of 10 µM. In FIG. 4, the position at which each primer hybridizes is shown by an arrowhead in the right-hand direction (5'-primer, SEQ ID NO: 5) and an arrowhead in the left-hand direction (3'-primer, SEQ ID NO: 6).

c) Amplification of Genomic DNA by LA-PCR Method

Genomic DNA is amplified by LA-PCR method. To the genomic DNA solution (1.0 µl) prepared in item a) mentioned above are added 25.8 µl of sterilized water, 8.0 µl of 2.5 mM dNTPs solution, 5.0 µl of a 25 mM magnesium chloride solution, 5.0 µl of 10×LA-PCR buffer, 2.5 µl of 10 µM sense primer (CYP2A6-B4), 2.5 µl of 10 µM antisense primer (CYP2A6-UTRAS1), and 0.2 µl of LA Taq DNA polymerase (5 U/µl, manufactured by Takara Shuzo Co., Ltd.) to make up an entire volume of 50 µl. Further, 50 µl of mineral oil was overlaid. After a denaturation reaction at 94° C. for 3 minutes, reactions are carried out in 30 cycles, wherein one cycle comprises 94° C. for 1 minute, 50° C. for 1 minute, and 72° C. for 2 minutes, and further an extension reaction at 72° C. for 10 minutes is carried out.

d) Determination Method

As a result of the above-mentioned LA-PCR, an amplified product having a size of about 1.3 kbp is obtained. The determination of presence or absence of the wild-type CYP2A6 is carried out on the bases of the findings that when each of these LA-PCR amplified products is digested with a restriction enzyme AccII, the conversion-type CYP2A6 (CYP2A6*1B) is cleaved into fragments having sizes of about 1.04 kbp and about 0.28 kbp, and the whole deletion-type CYP2A6 (CYP2A6*4C) is cleaved into fragments having sizes of about 1.02 kbp and about 0.28 kbp, but the wild-type CYP2A6 (CYP2A6*1A) was not cleaved (FIG. 4, FIG. 5a). The digestion by the restriction enzyme is carried out under the following conditions. To the reaction mixture (5.0 µl) after the termination of reaction of LA-PCR of item c) above are added 3.75 µl of sterilized water, 1.0 µl of 10×restriction enzyme M solution (Takara Shuzo Co., Ltd.), and 0.25 µl of AccII (8 U/µl, manufactured by Takara Shuzo Co., Ltd.) to make up an entire volume of 10 µl. The mixture is incubated at 37° C. for 10 hours. After the termination of reaction, the mixture is subjected to electrophoresis using 2% agarose gel containing 0.02% ethidium bromide, and the determination is made in comparison with size marker DNAs under UV irradiation.

On the other hand, when the LA-PCR amplified product having a size of about 1.3 kbp is digested with a restriction enzyme Eco81I, while the whole deletion-type CYP2A6 (CYP2A6*4C) is cleaved into fragments having sizes of about 0.73, 0.43, 0.1 and 0.04 kbp, each of the wild-type CYP2A6 (CYP2A6*1A) and the conversion-type CYP2A6 (CYP2A6*1B) is cleaved into fragments having sizes of about 0.79, 0.43, and 0.1 kbp (FIG. 4, FIG. 5b; provided that bands having sizes of 0.1 kb and 0.04 kb are almost not observed on the gel). The digestion by the restriction enzyme is carried out under the following conditions. To the reaction mixture (5.0 µl) after the termination of reaction of LA,-PCR of item c) above are added 3.5 µl of sterilized water, 1.0 µl of 10×restriction enzyme M solution (Takara Shuzo Co., Ltd.), and 0.5 µl of Eco81I (8 U/µl, Takara Shuzo Co., Ltd.) to make up an entire volume of 10 µl. The mixture is incubated at 37° C. for 10 hours. After the termination of reaction, the mixture is subjected to electrophoresis using 2% agarose gel containing 0.02% ethidium bromide, and the determination is made in comparison with size marker DNAs under UV irradiation.

Figure 6:
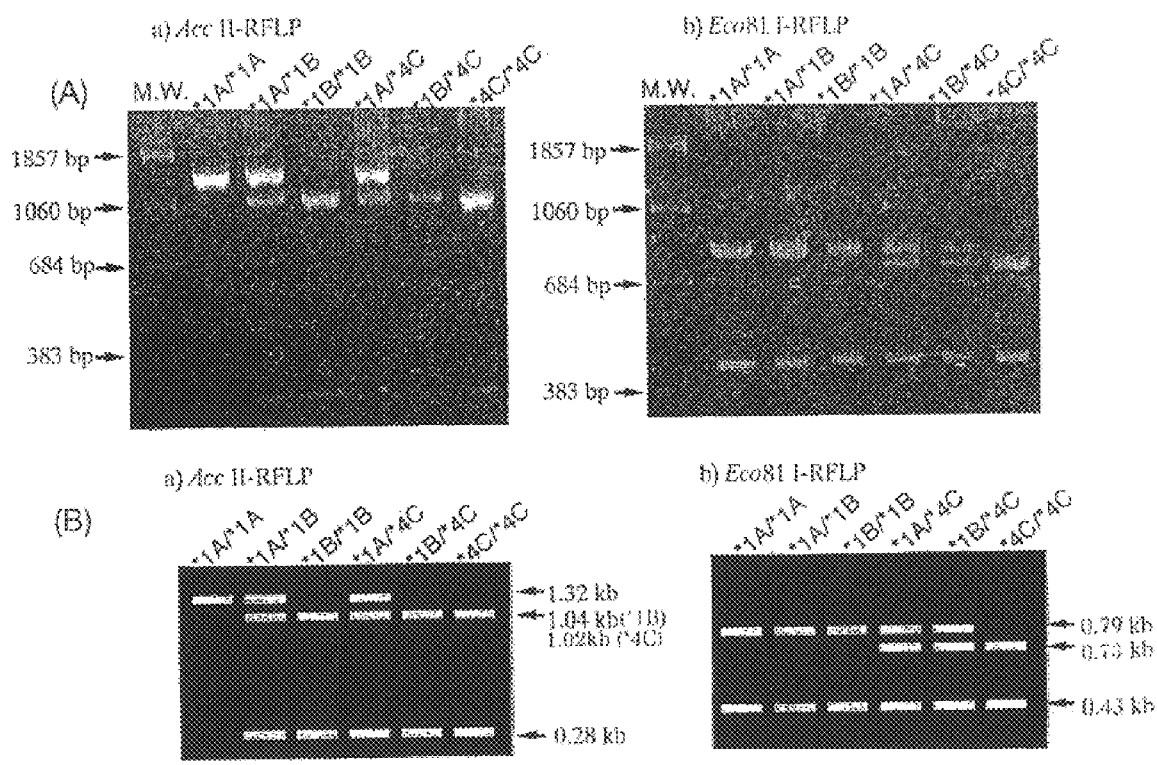
FIG. 6 is photographs of electrophoretic results for a) AccII-RFLP and b) Eco81I-RFLP of Japanese normal individuals [panel (A)], and their corresponding schematic views [panel (B)] according to the genotyping method of the present invention, wherein M.W. indicates size markers of DNA, and *1A/*1A, *1A/*1B, *1B/*1B, *1A/*4C, *4B/*4C and *4C/*4C represent genotypes of wild-type (CYP2A6*1A), conversion-type (CYP2A6*1B) and whole deletion-type (CYP2A6*4C).

Four-hundred and forty-four Japanese normal individuals were genotyped by using this novel diagnostic method. Examples of the resulting RFLPs are shown in FIG. 6, and the results thereof are summarized in Table 1. From FIG. 6, the diagnostic method of the present invention can differentiate all genotypes *1A/*1A, *1A/*1B, *1B/*1B, *1A/*4C, *1B/*4C and *4C/*4C, including wild-type (CYP2A6*1A), conversion-type (CYP2A6*1B) and whole deletion-type (CYP2A6*4C).

TABLE 1

Frequency Distribution of CYP2A6 Genotype and Allele in Japanese Normal Individuals

|  | Number | Frequency (%) |
|---|---|---|
| Genotype |  |  |
| Wild-type/Wild-type | 69 | 15.5 |
| Wild-type/Conversion-type | 153 | 34.5 |
| Conversion-type/Conversion-type | 74 | 16.7 |
| Wild-type/Whole Deletion-type | 68 | 15.3 |
| Conversion-type/Whole Deletion-type | 65 | 14.6 |
| Whole Deletion-type/ Whole Deletion-type | 15 | 3.4 |
| Total | 444 |  |
| Allele |  |  |
| Wild-type | 359 | 40.4 |
| Conversion-type | 366 | 41.2 |
| Whole Deletion-type | 163 | 18.4 |
| Total | 888 |  |

As shown in Table 1, from the fact that the frequency of the heterozygous deletion individuals (sum of wild-type/whole deletion-type and conversion-type/whole deletion-type) was almost identical to the frequency deduced upon calculation, it was clarified that this novel diagnostic method can accurately differentiate not only the homozygous deletion individual (whole deletion-type/whole deletion-type) but also the heterozygous deletion individual.

In addition, 239 French normal individuals were genotyped by using the same diagnostic method. The results are shown in Table 2.

TABLE 2

Frequency Distribution of CYP2A6 Genotype and Allele in European (French) Normal Individuals

|  | Number | Frequency (%) |
|---|---|---|
| Genotype |  |  |
| Wild-type/Wild-type | 99 | 41.4 |
| Wild-type/Conversion-type | 97 | 40.6 |
| Conversion-type/Conversion-type | 24 | 10.1 |
| Wild-type/Whole Deletion-type | 19 | 7.9 |
| Conversion-type/Whole Deletion-type | 0 | 0.0 |

TABLE 2-continued

Frequency Distribution of CYP2A6 Genotype and Allele in European (French) Normal Individuals

|  | Number | Frequency (%) |
|---|---|---|
| Whole Deletion-type/ Whole Deletion-type | 0 | 0.0 |
| Total | 239 | |
| Allele | | |
| Wild-type | 314 | 65.7 |
| Conversion-type | 145 | 30.3 |
| Whole Deletion-type | 19 | 4.0 |
| Total | 478 | |

As shown in Table 2, in French individuals, there existed no homozygous deletion individuals [i.e. homozygous individuals with whole deletion-type gene (whole deletion-type/whole deletion-type)] within the tested range. On the other hand, with regard to the conversion-type, the frequency of heterozygous deletion individuals [i.e. heterozygous individuals with conversion-type gene (wild-type/conversion-type and conversion-type/whole deletion-type)] was identical to the frequency theoretically calculated by the Hardy-Weinberg Law. Therefore, it was clarified that this diagnostic method can also accurately differentiate each genotype in Europeans.

SEQUENCE LISTING FREE TEXT

The oligonucleotide consisting of the nucleotide sequence of SEQ ID NO: 5 is 5'-primer designed for PCR.

The oligonucleotide consisting of the nucleotide sequence of SEQ ID NO: 6 is 3'-primer designed for PCR.

INDUSTRIAL APPLICABILITY

According to the diagnostic method of the present invention, each of wild-type, whole deletion-type and conversion-type CYP2A6 genes can be determined. Therefore, there is exhibited an excellent effect such that the treatment can be made depending upon a patient by previously diagnosing the individual differences in the metabolic ability of substances which are to be substrates for human CYP2A6.

What is claimed is:

1. A method for identifying a wild-type or a conversion-type cytochrome P4502A6 (CYP2A6) gene comprising the steps of:
   (a) obtaining genomic DNA containing a CYP2A6 gene from a human being; and
   (b) comparing said gene to the wild-type CYP2A6 gene and the conversion-type CYP2A6 gene wherein said conversion-type gene contains a substitution of about 60 bp of exon 9 of the CYP2A7 gene in place of the corresponding exon 9 sequences of the CYP2A6 gene,
   wherein if the comparison shows that said CYP2A6 gene is identical to said wild-type gene then said CYP2A6 gene is identified as a wild-type gene and if the comparison shows that said CYP2A6 gene is identical to said conversion-type gene then said CYP2A6 gene is identified as a conversion-type gene.

2. The method according to claim 1, wherein the conversion-type CYP2A6 gene comprises the nucleotide sequence of SEQ ID NO.: 4.

3. A method for identifying a wild-type a whole deletion-type, or a conversion-type CYP2A6 gene comprising the steps of:
   (a) obtaining genomic DNA containing a CYP2A6 gene from a human being; and
   (b) comparing said gene to the wild-type CYP2A6 gene, the whole deletion-type CYP2A6 gene that lacks exon 1–9, and the conversion-type CYP2A6 gene wherein said conversion-type gene contains a substitution of about 60 bp of exon 9 of the CYP2A7 gene in place of the corresponding exon 9 sequences of the CYP2A6 gene,
   wherein if the comparison shows that said CYP2A6 gene is identical to said wild-type gene then said CYP2A6 gene is identified as a wild-type gene; and if said comparison shows that said CYP2A6 gene is identical to said whole deletion-type gene, then said CYP2A6 gene is identified as a whole deletion-type gene; and if the comparison shows that said CYP2A6 gene is identical to said conversion-type gene then said CYP2A6 gene is identified as a conversion-type gene.

4. The method according to claim 3, wherein the whole deletion-type CYP2A6 gene comprises the nucleotide sequence of SEQ ID NO.: 1 and the conversion-type CYP2A6 gene comprises the nucleotide sequence of SEQ ID NO.: 4.

5. The method according to any one of claims 1 to 4, wherein said comparison is conducted by a method comprising PCR or hybridization.

6. The method according to any one of claims 1 or 2, wherein the method further comprises the following steps of:
   (1) preparing 5'-primer that hybridizes to both exon 8 of the CYP2A6 gene and exon 8 of the CYP2A7 gene, and 3'-primer that specifically hybridizes to exon 9 of the CYP2A6 gene;
   (2) conducting a PCR using the genomic DNA of step (a) as the template and the primers prepared in step (1) above;
   (3) digesting the amplified products obtained in step (2) with two kinds of restriction endonucleases; and
   (4) comparing the sizes of the resulting products of step (3) to the sizes of the fragments obtained by digesting with the restriction endonucleases the amplified products of the wild-type CYP2A6 gene and the conversion-type CYP2A6 gene obtained by conducting a PCR using the wild-type CYP2A6 gene and the conversion-type CYP2A6 gene as the templates, respectively, and the primers prepared in step (1) above.

7. The method according to any one of claims 3 or 4, wherein the method further comprises the following steps of:
   (1) preparing 5'-primer that hybridizes to both exon 8 of the CYP2A6 gene and exon 8 of the CYP2A7 gene, and 3'-primer that specifically hybridizes to exon 9 of the CYP2A6 gene;
   (2) conducting a PCR using the genomic DNA of step (a) as the template and the primers prepared in step (1) above;
   (3) digesting the amplified products obtained in step (2) with two kinds of restriction endonucleases; and
   (4) comparing the sizes of the resulting products of step (3) to the sizes of the fragments obtained by digesting with the restriction endonucleases the amplified products of the wild-type CYP2A6 gene, the whole deletion-type CYP2A6 gene and the conversion-type CYP2A6 gene obtained by conducting a PCR using the wild-type CYP2A6 gene, the whole deletion-type CYP2A6 gene and the conversion-type CYP2A6 gene as the templates, respectively, and the primers prepared in step (1) above.

8. The method according to claim 6, wherein said 5'-primer has the nucleotide sequence of SEQ ID NO.: 5, and said 3'-primer has the nucleotide sequence of SEQ ID NO.: 6.

9. The method according to claim 7, wherein, as a result of step (4), genotype of the said human being is determined to be a homozygous or a heterozygous deletion of CYP2A6.

10. The method according to claim 6, wherein the restriction endonucleases are AccII or an isochizomer thereof and Eco81I or an isochizomer thereof.

11. The method according to claim 5, wherein said comparison is conducted with a DNA fragment comprising at least 5 bp and at least bases 45–46 or 103–104 of SEQ ID NO.: 4.

12. The method according to claim 11, wherein said DNA fragment is bound to a solid support.

13. A conversion-type CYP2A6 gene comprising the nucleotide sequence of SEQ ID NO.: 4.

14. A DNA molecule consisting of the nucleic acid sequence of SEQ ID NO.: 6.

15. A diagnostic kit for determining a CYP2A6 genotype comprising: a 5'-primer that hybridizes to both exon 8 of the CYP2A6 gene and exon 8 of the CYP2A7 gene; a 3'-primer that specifically hybridizes to exon 9 of the CYP2A6 gene; AccII or an isochizomer thereof; and Eco81I or an isochizomer thereof.

16. The diagnostic kit according to claim 15, wherein said 5'-primer has the nucleotide sequence of SEQ ID NO.: 5, and said 3'-primer has the nucleotide sequence of SEQ ID NO.: 6.

17. A method for determining that a CYP2A6 gene is of the same length as that of a wild-type, a whole deletion-type, or a conversion-type CYP2A6 gene comprising the steps of:
   (a) obtaining genomic DNA containing a CYP2A6 gene from a human being;
   (b) preparing a 5'-primer having the nucleotide sequence of SEQ ID NO: 5 and a 3'-primer having the nucleotide sequence of SEQ ID NO: 6;
   (c) conducting a PCR using the genomic DNA of step (a) as the template, and the 5' primer and 3' primer of step (b);

(d) digesting the amplified products obtained in step (c) with AccII or an isochizomer thereof and Eco81I or an isochizomer thereof; and (e) comparing the sizes of the resulting products of step (d) to the sizes of the fragments obtained by digesting with AccII or an isochizomer thereof and Eco81I or an isochizomer thereof the amplified products of the wild-type CYP2A6 gene, and the whole deletion-type CYP2A6 gene that lacks exon 1–9, and the conversion-type CYP2A6 gene wherein said conversion-type gene contains a substitution of about 60 bp of exon 9 of the CYP2A7 gene in place of the corresponding exon 9 sequences of the CYP2A6 gene, which are obtained by conducting a PCR using the wild-type CYP2A6 gene, and the whole deletion-type CYP2A6 gene and the conversion-type CYP2A6 gene as the templates, respectively, and said 5' primer and 3'-primer of step (b), wherein if the comparison shows that said fragments produced from said CYP2A6 gene are identical in size to the fragments produced by said wild-type gene, then said CYP2A6 gene is identified as being the same length as said wild-type gene; and if said comparison shows that said fragments produced from said CYP2A6 gene are identical in size to said fragments produced by said whole deletion-type gene, then said CYP2A6 gene is identified as being the same length as said whole deletion-type gene; and if the comparison shows that said fragments produced from said CYP2A6 gene are identical in size to said conversion-type gene then said CYP2A6 gene is identified as being the same length as said conversion-type gene.

18. The method according to claim 17, wherein the whole deletion-type CYP2A6 gene comprises the nucleotide sequence of SEQ ID NO.: 1 and the conversion-type CYP2A6 gene comprises the nucleotide sequence of SEQ ID NO.: 4.

19. The method according to claim 38 or 39, wherein, as a result of step (e), genotype of the said human being is determined to be a homozygous or a heterozygous deletion of CYP2A6.

20. The method according to claim 28, wherein said 5'-primer has the nucleotide sequence of SEQ ID NO.: 5, and said 3'-primer has the nucleotide sequence of SEQ ID NO.: 6.

21. The method according to claim 29, wherein, as a result of step (4), genotype of the said human being is determined to be a homozygous or a heterozygous deletion of CYP2A6.

22. The method according to claim 28, wherein the restriction endonucleases are AccII or an isochizomer thereof and Eco81I or an isochizomer thereof.

23. The method according to claim 29, wherein the restriction endonucleases are AccII or an isochizomer thereof and Eco81I or an isochizomer thereof.

24. The method according to claim 30, wherein the restriction endonucleases are AccII or an isochizomer thereof and Eco81I or an isochizomer thereof.

25. A method for determining that a CYP2A6 gene is of the same length as that of a wild or mutant type CYP2A6 gene comprising the steps of:

(a) obtaining genomic DNA containing a CYP2A6 gene from a human being;

(b) preparing a 5'-primer having the nucleotide sequence of SEQ ID NO: 5 and a 3'-primer having the nucleotide sequence of SEQ ID NO: 6;

(c) conducting a PCR using the genomic DNA of step (a) as the template, and the 5' primer and 3' primer of step (b);

(d) digesting the amplified products obtained in step (c) with AccII or an isochizomer thereof and Eco81I or an isochizomer thereof; and (e) comparing the size of the resulting products of step (d) to the sizes of the fragments obtained by digesting with AccII or an isochizomer thereof and Eco81I or an isochizomer thereof the amplified products of the wild-type CYP2A6 gene which are obtained using the wild-type CYP2A6 gene as a template, and the 5'-primer and 3'-primer of step (b), wherein if the comparison shows that said fragments produced from said CYP2A6 gene are identical in size to the fragments produced by said wild-type gene, then said CYP2A6 gene is identified as being the same length as said wild-type gene; and if said comparison shows that said fragments produced from said CYP2A6 gene are different in size compared to said fragments produced by said wild-type gene, then said CYP2A6 gene is identified as being the same length as a mutant-type CYP2A6 gene.

* * * * *

SEQUENCE LISTING

```
<160> NUMBER OF SEQ ID NOS: 6

<210> SEQ ID NO 1
<211> LENGTH: 451
<212> TYPE: DNA
<213> ORGANISM: Homo sapiens

<400> SEQUENCE: 1
accatgagct tcctgccccg ctgagcgagg gctgtgccgg tgcaggtctg gtgggcgggg      60
ccagggaaag gcggggtcag ggcggggttc gcggaagagg cgggtataag aatgggggga     120
agatgcggga aaggaagggg cgtggtggct agagggaaga gaagaaacag aagggctca     180 gttcaccttg ataaggtgct tccgagctgg gatgagagga aggaaaccct tacattatgc    240
tatgaagagt agtaataata gcagctctta tttcctgagc acgtaccccc gtgtcaccttt    300 tgttcaaaaa ccattgcacg ctcacctaat tgccacaaac ctctgcgaag ggcgttcatg     360 cccatttttac acgtgacaaa actgaggctt agaaagttgt ctctgatgtc tcacaaaaca    420
taagtgccca gaaaatcttt gaacacagat c                                    451

<210> SEQ ID NO 2
<211> LENGTH: 466
<212> TYPE: DNA
<213> ORGANISM: Homosapiens

<400> SEQUENCE: 2
accatgagct tcctgccccg ctgagcgagg gctgtgccgg tgcaggtctg gtgggcgggg      60
ccagggaaag gcggggtcag ggcggggttc gcggaagagg cgggtataag aatgggggga     120
agatgcggga aaggaagggg cgtggtggct agagggaaga gaagaaacag aagggctca     180 gttcaccttg ataaggtgct tccgtggtgg gatgagagga aggaaaccct tacattatgc    240
tatgaagagt agtaataata gcagctctta tttcctgagc acgtaccccc gtgtcaccttt    300 tgttcaaaaa ctattgcacg ctcacctcac ttaattgcca caacctctg cgaagggggaa    360 aagcgttcat gcccatttta cacgtgacaa agctgaggct tagaaagttg gctctatctg    420
```

```
atgtctcaca aaacataagt gcccagaaaa tctttgaaca cagatc         466
```

<210> SEQ ID NO 3
<211> LENGTH: 428
<212> TYPE: DNA
<213> ORGANISM: Homo sapiens
<400> SEQUENCE: 3

```
gcgagggctg tgccggtgca ggtctggtgg gcggggccag ggaaagggca gggccaagac    60
cgggcttggg agaggggcgc agctaagact gggggcagga tggcggaaag gaagggggcgt  120
ggtggctaga gggaagagaa gaaacagaag cggctcagtt caccttgata aggtgcttcc  180
gagctgggat gagaggaagg aaaccttac attatgctat gaagagtagt aataatagca   240
gctcttattt cctgagcacg tacccccgtg tcacctttgt tcaaaaacca ttgcacgctc  300
acctaattgc cacaaacctc tgcgaagggc gttcatgccc attttacacg tgacaaaact  360
gaggcttaga aagttgtctc tgatgtctca caaaacataa gtgcccagaa aatctttgaa  420
cacagatc                                                           428
```

<210> SEQ ID NO 4
<211> LENGTH: 427
<212> TYPE: DNA
<213> ORGANISM: Homo sapiens
<400> SEQUENCE: 4

```
gcgagggctg tgccggtgca ggtctggtgg gcggggccag ggaaaggcgg ggtcagggcg    60
gggttcgcgg aagaggcggg tataagaatg ggggaagat gcgggaaagg aagggggcgtg  120
gtggctagag ggaagagaag aaacagaagc ggctcagttc accttgataa ggtgcttccg  180
agctgggatg agaggaagga aaccttaca ttatgctatg aagagtagta ataatagcag   240
ctcttatttc ctgagcacgt accccgtgt cacctttgtt caaaaaccat tgcacgctca   300
cctaattgcc acaaacctct gcgaagggcg ttcatgccca ttttacacgt gacaaaactg  360
aggcttagaa agttgtctct gatgtctcac aaaacataag tgcccagaaa atctttgaac  420
acagatc                                                            427
```

<210> SEQ ID NO 5
<211> LENGTH: 22
<212> TYPE: DNA
<213> ORGANISM: Artificial Sequence
<220> FEATURE:
<223> OTHER INFORMATION: 5' primer directed to Homo sapiens
<400> SEQUENCE: 5

```
caccgaagtg ttccctatgc tg                                           22
```

<210> SEQ ID NO 6
<211> LENGTH: 22
<212> TYPE: DNA
<213> ORGANISM: Artificial Sequence
<220> FEATURE:
<223> OTHER INFORMATION: 3' primer directed to Homo sapiens
<400> SEQUENCE: 6

```
tgtaaaatgg gcatgaacgc cc                                           22
```